United States Patent
Hernandez Romero et al.

(10) Patent No.: US 9,801,388 B2
(45) Date of Patent: Oct. 31, 2017

(54) METHOD FOR A PESTICIDE HAVING AN INSECTICIDE, ACARICIDE AND NEMATICIDE ACTION BASED ON ISOQUINOLINE ALKALOIDS AND FLAVONOIDS

(71) Applicant: PROMOTORA TECNICA INDUSTRIAL, S.A. DE C.V., Jiutepec, Estado de Mexico (MX)

(72) Inventors: Yanet Micahela Hernandez Romero, Estado de Mexico (MX); Cristina Margarita Rodriguez Narvaez, Estado de Mexico (MX); Mario Saavedra Aguilar, Estado de Mexico (MX)

(73) Assignee: PROMOTORA TECNICA INDUSTRIAL, S.A. DE C.V., Jiutepec, Estado de Mexico (MX)

( * ) Notice: Subject to any disclaimer, the term of this patent is extended or adjusted under 35 U.S.C. 154(b) by 43 days.

(21) Appl. No.: 15/014,817

(22) Filed: Feb. 3, 2016

(65) Prior Publication Data
US 2017/0156345 A1     Jun. 8, 2017

Related U.S. Application Data

(63) Continuation of application No. 13/636,330, filed on Sep. 5, 2013, now abandoned.

(30) Foreign Application Priority Data

Sep. 23, 2011   (MX) .................. MX/a/2011/010032

(51) Int. Cl.
| | |
|---|---|
| A01N 65/08 | (2009.01) |
| A01N 65/12 | (2009.01) |
| A01N 65/32 | (2009.01) |
| A01N 65/00 | (2009.01) |
| A01N 43/42 | (2006.01) |

(52) U.S. Cl.
CPC ............. *A01N 65/12* (2013.01); *A01N 43/42* (2013.01); *A01N 65/00* (2013.01); *A01N 65/08* (2013.01); *A01N 65/32* (2013.01)

(58) Field of Classification Search
None
See application file for complete search history.

(56) References Cited

U.S. PATENT DOCUMENTS

| | | |
|---|---|---|
| 6,372,239 B1 | 4/2002 | Wu et al. |
| 2005/0244445 A1 | 11/2005 | Anderson |
| 2008/0300225 A1 | 12/2008 | Marrone |
| 2015/0216181 A1 | 8/2015 | Hernandez Romero |

FOREIGN PATENT DOCUMENTS

CN   2004-10022134   9/2005

OTHER PUBLICATIONS

Wu, Tianran Chanwu Yanjiu Yu Kaifa (2009), 21(3), p. 430-432, English abstract only.
Gertig, Acta Poloniae Pharmaceutica (1957), 14, 101-8, English abstract only.
Xue, CN 1672520A, Sep. 28, 2005, machine translation.
Wei, Zhongchengyao (2010), 32 (3), 359-362, English abstract only.

*Primary Examiner* — Layla D Berry
(74) *Attorney, Agent, or Firm* — Andrew W. Chu; Craft Chu PLLC

(57) ABSTRACT

The method for a pesticide having an insecticide, acaricide and nematicide action is obtained from plant extracts that have important synergic interactions in pesticide activity. The characteristics of the pesticide are efficient control of insects, mites and nematodes, low toxicity for mammals and low persistence in the environment. This pesticide is a composition based on plant extracts containing isoquinoline alkaloids and their derivatives (0.1-20%) and flavonoids and their glycosylated derivatives (0.001-10%). Therefore, the field of the invention is generally organic pesticides and in particular to obtaining an organic pesticide which contains, as an active ingredient, a mixture of isoquinoline alkaloids and flavonoids to be used to control agricultural pests.

8 Claims, No Drawings

METHOD FOR A PESTICIDE HAVING AN INSECTICIDE, ACARICIDE AND NEMATICIDE ACTION BASED ON ISOQUINOLINE ALKALOIDS AND FLAVONOIDS

CROSS-REFERENCE TO RELATED APPLICATIONS

See Application Data sheet

The present application claims continuation priority under 35 U.S.C. Section 120 from U.S. Ser. No. 13/636,330, filed on 20 Sep. 2012, entitled "PESTICIDE HAVING AN INSECTICIDE, ACARICIDE AND NEMATICIDE ACTION BASED ON ISOQUINOLINE ALKALOIDS AND FLAVONOIDS".

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a pesticide having an insecticide, acaricide and nematicide action which at least includes an isoquinoline alkaloid and at least a flavonoid, same produce important synergic interactions in their biological activity, said invention is efficient to control plagues and its main characteristics are: high specificity on target plagues, low toxicity for mammals, low persistence in the environment and in which the active ingredients could come, although not exclusively, from plant extracts.

Likewise, the present invention relates to a manufacturing process, consisting of two stages, where the first stage refers to obtaining and standardizing the active principles of the pesticide: isoquinoline alkaloids and flavonoids, as well as a second stage related to its commercial formula.

2. Description of Related Art Including Information Disclosed Under 37 CFR 1.97 and 37 CFR 1.98.

Historically, the first generation of botanical pesticides dates back to the XIX Century, when some compounds of a botanical origin such as alkaloids, rotenone and rotenoid compounds, pyrethrins and essential oils were identified.

Alkaloids are nitrogenous secondary metabolites, generally of a basic character and most of these compounds are biosynthetized from amino acids. Nicotine is an alkaloid isolated from the tobacco plant, mainly form *Nicotiana tabacum* and *Nicotiana rustica* (Solanaceae), and it is considered as a toxic and dangerous pesticide for humans. It is a neurotoxin that specifically acts on the nicotinic cholinergic receptors by delaying the closing of the sodium channels, this causes paralysis before death.

Sabadilla is a pesticide obtained from the *Schoenocaulon officinale* seeds. Its active principles are mainly the cevadine, veratridine alkaloids, which are esters of a steroidal alkaloid called veracevine which are toxic for mammals ($DL_{50}$ 13 mg/kg), but in commercial preparations that include it as an active ingredient its concentration is less than 1%. The mechanism action of this type of alkaloids is similar to that of pyrethrins.

Ryania is a powder obtained from the *Ryania speciosa* Wood and its activity is attributed to the ryanodine (<1%), a pyrrole-2-carboxylic ester of a complex diterpene (ryanodol). Ryanodine acts as a pesticide interfering with calcium release in the muscular tissue causing a sharp muscular contraction which can be followed by paralysis.

Rotenone is an isoflavonoid and the main pesticide component of the roots or rhizomes of the tropical leguminous *Derris, Lonchocarpus* and *Tephrosia*. Most of the rotenone used at present comes from *Lonchocarpus*, also known as cube root. About 44% of rotenone and 22% of deguelin, another rotenoid is extracted from this root. Rotenone is a mitochondrial poison which blocks electron transportation and prevents the production of energy. Rotenone is toxic for humans ($DL_{50}$ 132 mg/kg) and although commercial formulations use less toxic levels than those of lethal doses, this pesticide has a limited use in agriculture.

Pyrethrum is extracted from the *chrysanthemum* flowers (*Tanacetum cinerarifolium*, Asteraceae) and it is a mixture of 6 secondary metabolites: pyrethrins I and II, cinerin I and II and jasmolins I and II. Pyrethrum is a neurotoxin that causes immediate paralysis in insects because it blocks voltage sodium channels that depend on axons. This action mechanism is similar to that of the organochlorate pesticide DDT, but as opposed to this, pyrethrins show moderate toxicity for mammals. In spite of its immediate action, most of the insects recover, unless pyrethrum is formulated with a synergic agent. Pyrethrum constitutes approximately 80% of the total of commercial botanical pesticides in the world.

Essential oils are the main volatile aromatic principles of plants, of a complex chemical nature that mainly include terpenoids, where monoterpenes are the biggest group and the sesquiterpenes appear in a smaller proportion (these contain 10 and 15 carbon atoms, respectively) and more rarely diterpenes (20 carbon atoms). Essential oils, mainly monoterpenes are specifically toxic against pest insects due to their neurotoxic mechanism which acts on the octopaminergic receptors in the system which transmits nervous impulses in invertebrates. Essential oils due to their volatile nature probably enter the insect through the respiratory system and at present are mainly used to protect domestic animals and clothes (against moths), and also as wood preservatives.

Phytosanitary products of a plant origin in this first generation were substituted by pesticides product of chemical synthesis as organochlorate compounds, organophosphorus and carbamates, which caused severe environmental contamination problems and resistance in insects, in addition to harmful effects in non-target organisms. As an answer to all of these problems a strictly chemical strategy arose where the modification of the structure of natural products was sought for to obtain compounds that would have better pesticide activity and less toxicity for mammals, these search originated pyrethroids. The interest to develop products of a plant origin was also importantly renewed, and chemical ecology emerged where chemists, biochemists, toxicologists and specialists in plant protection joined efforts in the research of natural products of a botanical origin to control pest with a minimum of environmental problems. This established the rules for the second generation of botanical pesticides.

The more detailed study of the relationship between plants and insects, allowed researches to know that evolution has given plants chemical mediators implied in the communication between species, same that are known as semiochemical compounds which are regarded as non-nutritious compounds produced by an organism that affect behavior or the biology of individuals of the same species (pheromones) or of different species (allelochemical molecules). The latter have a series of effects before harmful insects and are classified according to their mode of action as defensive, toxic, repellent or discouraging, antiphagostimulant or digestive inhibitors, and attracting substances, among others, and depending on their chemical composition and intensity they reveal information in respect to the physiological status of the plant and the stress in which it is and modify behavior or the biology of an organism of another species. These molecules generally act at a low dose and have a specific action and their toxicity for mammals is low.

This second generation of botanical pesticides allowed western researches to rediscover neem used in India since ancestral times. From the neem tree seeds (*Azadirachta indica*, Meliaceae) two kinds of pesticides can be obtained: Neem oil (essential oil) and azadirachtin (10-25%), a limonoid of the meliacine type. Limonoids have mainly been isolated from the Meliaceae (meliacines) and Rutacea (limonoids of citric plants) families. Limonoides are modified triterpenes or tetranortriterpenoids, highly oxygenated derived from the 4,4,8-trimethyl-17-furanosylsteroid precursor. Limonoids of the meliacine type are structurally more complex than limonoids from citrus plants and have a higher oxidation level. Azadirachtin carries out its pesticide action by blocking synthesis and hormone release during ecdysis of mature insects which as a consequence inhibits their growth and development, and in adult insects, through a similar mechanism, causes sterility. Azadirachtin is also a powerful antifeedant.

In the last few years greater acceptance in the world market of new alternatives for the integral management of plants has been observed, due to the resistance developed by insects and to other undesirable side effects originated by the indiscriminate use of conventional synthetic pesticides. But, on the other hand there are also several factors that limit the use of botanical pesticides because of inconsistent practical results probably caused by the lack of chemical standardization of the formulations; the non-competitive price compared to that of classic pesticides; and inappropriate formulations and application against a limited range of pest.

In previous works on botanical pesticide related to the present invention, patent US2005/0244445 was found, same makes reference to the synergic effect on insecticide activity of formulations based on essential oils, insecticide soaps and/or pyrethrins, with detergents such as sodium lauryl sulfate (SLS), sodium docedyl sulfate (SDS) or lecithin.

On the other hand, in American patents U.S. Pat. No. 6,372,239 and US2008/0300225 the use of tetracycle quinolizidinic alkaloids: matrine and oxymatrine, isolated in the roots of *Sophora*, individually or present in a mixture of alkaloids to carry out a synergetic effect on pest control is described. The pesticide activity of these alkaloids is attributed to its inhibition effect on the acetylcholinesterase enzyme, thus inhibiting degradation of the acetylcholine neurotransmitter. When the concentration of acetylcholine is increased, hyperexcitability of the Central Nervous System is caused; this originates the death of insects.

In addition, Stermitz et. al. (2002), reported the synergetic effect of two flavones: chrisosplenetine and chrysosplenol D (isolated from *Artemisia annua* L. extract) in the antimicrobial activity shown by berberine against *Staphylococcus aureus*. It was determined that these flavonoids block berberine extrusion from the bacterial cell by inhibiting the multidrug efflux (MDF) pump, thus allowing them to carry out their bactericide action.

Lastly, Chinese patent CN 2004-10022134 describes the process to manufacture a pesticide to prevent diseases in plants caused by pathogenic micro-organisms and to promote plant growth, which has as active ingredients a mixture of 0.06%-0.26% of berberine hydrochloride; 0.01-0.06% of matrine and 0.23-1.38% of flavonoids.

In this sense, the present invention refers to obtaining and manufacturing a pesticide having an insecticide, acaricide and nematicide action, new and efficient for integrated pest management which attack plants, fruits and/or animals, based on a new mixture of isoquinoline alkaloids and flavonoids from, although not exclusively, plant extracts that show important synergic interactions in their pesticide activity.

The isoquinoline alkaloids of the present invention may come from, although not exclusively, the Papaveraceae family and the flavonoids from the Asteraceae family. Both types of secondary metabolites can also be chemically synthesized.

In the Papaveracea family, the presence of isoquinoline alkaloids is known; said derive from protoberberine, tetrahydroberberine, protopine and benzophenanthridine, and spirobenzylisoquinoline and cularine in Fumarioideae, as well as from other groups that give them their known pharmacological properties: derived from aporphine, morphinane, pavine, isopavine, narceine and rhoeadine. At least other 20 alkaloids in plants belonging to this family are know; these are: cheilanthifoline, chelerytrine, N-norchelerytrine, dihydrochelerytrine, coptisine, cryptopine dihydrosanguinarine, norsanguinarine, scoulerine, stylopine, muramine, thalifoline, reframidine and oxyhydrastinine. These secondary metabolites are responsible for the medicinal properties attributed to the family.

In the Asteraceae family, especially of the genus *Cirsium*, a series of compounds having a pesticide activity of a different chemical nature have been isolated; these include flavonoids, sterols, triterpenes, alkaloids, polyacetylenes, acetylenes, sesquiterpenes, lactones, phenolic acids and lignans. Within the flavonoids isolated from *Cirsium*, glycosylated derivatives of apigenin, cirsimaritin, campherol, linarin, luteolin, pectolinarin y quercetin are included.

BRIEF SUMMARY OF THE INVENTION

The present invention is related in general to the biorational use of pesticides of botanical origin to the integral management of pest and particularly to the use of plant extracts, same which mainly include isoquinoline alkaloids and flavonoids as active secondary metabolites.

On this basis, the main object of the present invention is the incorporation of plant extracts for integrated pest management, consequently it does not imply risks to the environment, considering they are biodegradable substances therefore, persist for a short period in the environment and thus do not pollute and provide a biorational alternative to the use of conventional chemical pesticides.

An object of the present invention is that the mixture of plant extracts and their chemical composition allow it to carry out its pesticide activity on insects, mites and nematodes through different action mechanisms.

Another purpose of the present invention is that the plant extracts used in its formulation are constituted by a set of active principles, chemically different among themselves. This reduces the probability of target organisms to develop resistance to them.

An additional object of the present invention is to provide a pesticide having a combination of ingredients which have synergic properties; this reduces the amount of active ingredients without affecting the biological effectiveness against pest and provides low toxicity for mammals.

BRIEF DESCRIPTION OF THE SEVERAL VIEWS OF THE DRAWINGS

None.

DETAILED DESCRIPTION OF THE INVENTION

The present invention incorporates a procedure to obtain a pesticide having an insecticide, acaricide and nematicide action based on plant extracts which contain as active principles isoquinoline alkaloids and flavonoids, the efficiency of which lies in presenting a synergic effect in the integral management of pest.

Alkaloids can be obtained from plants such as those belonging to the Papaveraceae family that can be from the genus *Argemone*. Alternatively, the alkaloids in the present composition can also be chemically synthesized on an industrial scale. The level of extraction and the degree of purity of the alkaloids may vary, for example, integral extracts of plants, not purified can be used in the present invention. Depending on the solubility of the plant alkaloids, the extraction process for each alkaloid can differ; water or an organic solvent can be used. As an alternative, alkaloids can be fully or partially purified. The chemical synthesis of alkaloids obviates the need of extraction and purification.

The formulation can contain one of more alkaloids of the isoquinoline type and their derivatives, such as: berberine, protopine, allocryptopine, cryptopine, sanguinarine, dihydrosanguinarine, norsanguinarine, oxysanguinarine, 6-acetonyldihydrochelerythrine, dihydrochelerythrine, chelerythrine, N-norchelerythrine, chelerythridimerine, cheilanthifoline, coptisine, cryptopine, scoulerine, stylopine, muramine, thalifoline, reframidine and oxyhydrastinine.

Flavonoids, referred to in the pesticide of the present invention, can be synthesized or obtained from several plant species of the Asteraceae family, specifically of the genus *Cirsium*. These flavonoids belong to the group of flavonols, flavones and isoflavones and also include their glycosylated derivatives, specifically glycosides of apigenin, cirsimaritin, campherol, linarin luteolin, pectolinarin and quercetin.

All of the above mentioned metabolites can be obtained through biotechnological processes.

Extraction of the plant material in the present invention can carry out, although not exclusively, using approved solvents included in the 4 EPA list or through extraction with supercritrical fluids.

To obtain the pesticide with an insecticide, acaricide and nematicide action in the present invention two stages must be completed. In the first stage botanical extracts are obtained, and in the second the extracts are mixed with the necessary adjuvants to maintain a stable physicochemical formulation.

In this manner, the chemical composition of the present invention is composed of the combination or the mixture of the following ingredients:

| | |
|---|---|
| Isoquinoline alkaloids and their derivatives | 0.1-20% |
| Flavonoids and their glycosylated derivatives | 0.001-10% |

As part of the development of the present invention two examples of the pesticide formulations are presented, same which combine the active principles in different proportions and the efficacy of which was fully verified with evaluations against different pest organisms, both in the laboratory and on the field.

EXAMPLE 1

Process to Prepare Formulation 1

Step 1 Obtaining Plant Extracts (a) Process to Extract Alkaloids from *Argemone* Spp.

The extraction method using an organic solvent was used to obtain alkaloids from plant matter.

In this example, dry plant material from the species *Argemone* spp. (Papaveraceae) was loaded in a reactor and an organic solvent was added. The extraction process was carried out within a temperature range of 30 to 70° C., preferably during 1-6 h to later, unload the extract. The extract was concentrated by controlled distillation until a 0.01 to 30% concentration was obtained. The extract was unloaded and stored in a cool and dry area at 25° C. The alkaloid yield from a plant extract is about 5 to 15%.

(b) Extraction of Flavonoids from *Cirsium* Spp.

Flavonoid extraction was performed in an analog manner to the process to obtain the alkaloids described above. The dry plant matter, ground and weight of *Cirsium* spp. is loaded in a reactor provided with heating and agitation, an organic solvent is added, and the mixture is agitated preferably from 1 to 6 h, keeping the temperature at 40 to 70° C. The extract obtained with this process is filtered, unloaded and stored in polyethylene containers in a cool area at 25° C. The flavonoid yield obtained from the plant extract is about 0.5% to 10%.

Step 2 Process to Manufacture Formulation 1

To obtain the extract basis of the formulation the active extracts obtained from *Argemone* spp. and of *Cirsium* spp. are mixed. To do so, the extracts are loaded in the homogenizer and are agitated preferably from 1 to 3 h. It is unloaded and the pesticide is formulated.

To prepare the formulation, the extracts, the adjuvants and the solvents are weighed and then are loaded in the homogenizer reactor in such a way that the following proportions are kept: from 0.01 to 30% of the base extract, 1-10% of adjuvants and the remainder is water. The mixture is agitated preferably during a period of 1-3 h, until a homogeneous stable solution is obtained. The reactor is unloaded and the formulation is placed in containers.

EXAMPLE 2

Process to Prepare Formulation 2

Step 1 Preparation of Plant Extracts (a) Process to Extract Alkaloids from a Mixture of Plant Material The extraction of isoquinoline alkaloids can be from different species of the Papaveracea family. For this process, an appropriate amount of *Argemone* spp. and *Bocconia* spp. are weighed, these are placed in a reactor with a controlled temperature and an organic solvent is added. The extraction preferably is carried out at a temperature of 40 to 70° C. and it is kept in strong agitation during 1-6 h. The extract is unloaded, filtered and concentrated through distillation until a 0.01 to 30% concentration is obtained. The extract is unloaded and stored in a cool area at 25° C. The alkaloid yield from the plant extract is about 5 to 15%.

(b) Extraction of Flavonoids from De *Cirsium* Spp.

The process to extract flavonoids is the same as that described for formulation 1.

Step 2 Process to Manufacture Formulation 2

The preparation of the base extract is carried out. The extracts from *Argemone* ssp., *Bocconia* sp., and *Cirsium* spp. are mixed. Then, the extracts are loaded into a homogenizer reactor and they are agitated during 1-3 h. The reactor is unloaded and the pesticide product is formulated.

To obtain formulation 2 the active extracts, the adjuvants and the solvents are weighed and they are loaded in the homogenizer reactor in such a way that the following proportions are obtained: from 0.01 to 30% of the base extract, and from 1-10% of adjuvants and the remainder is water. This is agitated during 1-3 h until a stable homogeneous solution is obtained. The formulation is unloaded and then it is placed in containers.

Examples of the Evaluation of the Pesticide Formulations:

Field evaluation of two botanical formulations, formulation 1 and formulation 2, were carried out in different crops and against different species of pest insects. The results of the evaluation carried out in the laboratory are included.

The evaluation was carried out using a crop of *Cucurbita pepo* L., infested with insects of the genus *Bemisia*. The results of two applications are shown in Table I.

TABLE I

Field Evaluation of effectiveness against insects of the genus *Bemisia*

| Treatment | Dose | Effectiveness % |
|---|---|---|
| Formulation 1 | 5 mL/L | 61.3 |
| Formulation 2 | 5 mL/L | 61.7 |
| Water | — | 0 |

In accordance with the effectiveness percentages mentioned above, both of the developed products show a significant effectiveness to control insects belonging to the genus *Bemisia*. The evaluation was carried out four days after the application. The formulations were also applied to observe their effectiveness in the crop of *Citrus* sp. in controlling two pest species: *Diaphorina* sp. (adult and nymph) and mites of the genus *Polyphagotarsonemus*.

Table II shows the percentage of biological effectiveness of the formulations that were studied, in comparison to the dimethoate organophosphate insecticide and the absolute control, to control *Diaphorina* sp adults. Table III describes the effectiveness of the above mentioned treatments in controlling *Diaphorina* sp. nymphs.

TABLE II

Field evaluation of effectiveness against *Diaphorina* sp adults

| Treatment | Dose | Effectiveness % |
|---|---|---|
| Formulation 1 | 5 mL/L | 80.2 |
| Formulation 2 | 5 mL/L | 86 |
| Dimethoate | 5 mL/L | 100 |
| Water | 5 mL/L | 0 |

TABLE III

Field evaluation of effectiveness against *Diaphorina* sp nymphs

| Treatment | Dose | Effectiveness % |
|---|---|---|
| Formulation 1 | 5 mL/L | 78.6 |
| Formulation 2 | 5 mL/L | 94.6 |
| Dimethoate | 5 mL/L | 100 |
| Water | 5 mL/L | 0 |

In both cases the effectiveness percentage of the samples that were studied was satisfactory. It is observed that formulation 2 results in a higher mortality percentage in both biological stages.

Table IV describes the control percentages of the products for mites belonging to the genus *Polyphagotarsonemus*.

TABLE IV

Field evaluation of effectiveness against mites of genus *Polyphagotarsonemus*

| Treatment | Dose | Effectiveness % |
|---|---|---|
| Formulation 1 | 5 mL/L | 86.2 |
| Formulation 2 | 5 mL/L | 87.9 |
| Water | — | 0 |

Compared to the control which showed a 0% mortality percentage, the evaluated products showed a significant control level in mites of the genus *Polyphagotarsonemus* in *Citrus* sp.

With the *Brassica oleracea* crop assessments of the control of larvae of the *Plutella* genus was performed, the results of this assessment are shown in Table V. The assessment was carried out the fourth day after the application.

TABLE V

Field evaluation of effectiveness against larvae of genus *Plutella*

| Treatment | Dose | Effectiveness % |
|---|---|---|
| Formulation 1 | 5 mL/L | 29.6 |
| Formulation 2 | 5 mL/L | 47.2 |
| Spinosad | 100 mL/Ha | 52.8 |
| Water | 5 mL/L | 0 |

Formulation 2 showed better biological effectiveness, although it was less than that of the commercial control.

In all of the evaluations performed it was not observed that the developed products caused any harm to the crops on which they were applied.

In the laboratory assay both products were diluted to 5 mL of the formulation in 1 L of distilled water, and they were applied against insects of the genus *Bemisia*. To compare the effectiveness of the formulation distilled water was also applied as an absolute control and bifenthrin ([1a,3a-(Z)]-(±)-(2methyl[1,1'-biphenyl]-3-il)methyl-3-(2-cloro-3,3,3-trifluorine-1-propenyl-2,2-dimethyl cyclopropanecarboxylate) was applied as a commercial control. The application of the formulation was performed in laboratory conditions using devices to keep the specimens under observation. The effectiveness evaluation was carried out 24 hours after the application.

The experimental unit consisted of four devices that were kept at 26 (±2° C.). Three repetitions of each evaluation were performed.

In Table VI, the effectiveness observed in insects of the genus *Bemisia* after 24 hours of observation with each of the treatments is detailed. The dose of the commercial control (Bifenthrin) was that recommended by the manufacturer.

TABLE VI

In vitro evaluation of effectiveness against insects of the genus *Bemisia*

| Treatment | Dose | Effectiveness % |
| --- | --- | --- |
| Formulation 1 | 5 mL/L | 74.17 |
| Formulation 2 | 5 mL/L | 74.17 |
| Bifenthrin | 2 mL/L | 97.18 |
| Water | 5 mL/L | 0 |

The nematicide capacity of formulation 2 was evaluated; a satisfactory percentage after 48 hours was obtained. Nematodes of the genus *Meloidogyne* were used as target organism and the results are shown in Table VII.

TABLE VII

In vitro evaluation of effectiveness against nematodes of the genus *Meloidogyne*

| Treatment | Dilution | Effectiveness % |
| --- | --- | --- |
| Formulation 1 | 1:10 | 84.29 |
| Formulation 2 | 1:100 | 33.93 |
| Carbofuran | 1:200 | 100 |
| Water | — | 0 |

Based on the interpretation of the above described data for the different species and crops mentioned, it is concluded that formulations 1 and 2 are adequate to control sucking insects (*Bemisia* spp.), phytophagous mites, insects belonging to the genus *Diaphorina*, and phytopatogenic nematodes of the genus *Meloidogyne* because the mortality percentages that were observed are satisfactory.

We claim:

1. A method for producing a pesticide composition with insecticidal, acaricidal, and nematicidal properties, said method comprising the steps of:
   forming a concentrated alkaloid extract having a yield of 5-15%, the step of forming said concentrated alkaloid extract comprising the steps of:
     loading dry plant material from species of genus *Argemone* in a reactor;
     adding an organic solvent;
     forming an alkaloid extract by an extraction process within a temperature range of 30 to 70° C.;
     separating said alkaloid extract;
     concentrating said alkaloid extract to a 0.01-30% by weight through a controlled distillation so as to form a concentrated alkaloid extract;
     separating said concentrated alkaloid extract; and
     storing said concentrated alkaloid extract at 25 degrees C.;
   forming a concentrated flavonoid extract having a yield of 0.5-10%, the step of forming said concentrated flavonoid extract comprising the steps of:
     loading dry plant material from species of genus *Cirsium* in a reactor;
     adding an organic solvent;
     forming a flavonoid extract by an extraction process within a temperature range of 40 to 70° C. with agitation;
     separating said flavonoid extract;
     concentrating said flavonoid extract to a 0.01-30% by weight through a controlled distillation so as to form a concentrated flavonoid extract;
     separating said concentrated flavonoid extract; and
     storing said concentrated flavonoid extract at 25 degrees C.;
   forming a base extract comprised of 0.01-20% of said concentrated alkaloid extract and 0.001-10% of said concentrated flavonoid extract;
   mixing 0.01 to 30% of the base extract, 1-10% of adjuvants and 98.99-60% water in a homogenizer reactor so as to form a mixture; and
   agitating said mixture so as to obtain a homogeneous stable solution.

2. The method for producing said pesticide composition, according to claim 1, wherein the step of forming said alkaloid extract by an extraction process within said temperature range of 30 to 70° C. lasts 1-6 hours.

3. The method for producing said pesticide composition, according to claim 1, wherein the step of forming said flavonoid extract by an extraction process within said temperature range of 40 to 70° C. with agitation lasts 1-6 hours.

4. The method for producing said pesticide composition, according to claim 1, wherein the step of mixing 0.01 to 30% of the base extract, 1-10% of adjuvants and water 98.99-60% water in a homogenizer reactor so as to form a mixture, further comprising the step of:
   agitating said mixture for 1-3 hours.

5. The method for producing said pesticide composition, according to claim 1, wherein the step of forming said alkaloid extract by an extraction process within said temperature range of 30 to 70° C. lasts 1-6 hours with agitation.

6. The method for producing said pesticide composition, according to claim 1, wherein the step of forming said flavonoid extract by an extraction process within said temperature range of 40 to 70° C. with agitation lasts 1-6 hours.

7. A method for controlling pests in plants and animals, said method comprising the steps of:
   forming a homogeneous stable solution according to claim 1; and
   applying said homogeneous stable solution on an organism, said organism being selected from a group consisting of: a plant and an animal.

8. A method for controlling insects, said method comprising the steps of:
   forming a homogeneous stable solution according to claim 1; and
   applying said homogeneous stable solution in a domocile.

* * * * *